(12) United States Patent
Larsson et al.

(10) Patent No.: US 6,660,278 B1
(45) Date of Patent: Dec. 9, 2003

(54) CONTROLLED RELEASE COMPOSITION

(75) Inventors: Kåre Larsson, Bjärred (SE); Helena Ljusberg-Wahren, Höllviken (SE); Niels Krog, Bradbrand (DK)

(73) Assignee: GS Development AB, Malmö (SE)

(*) Notice: Subject to any disclaimer, the term of this patent is extended or adjusted under 35 U.S.C. 154(b) by 0 days.

(21) Appl. No.: 09/341,294

(22) PCT Filed: Jan. 8, 1998

(86) PCT No.: PCT/SE98/00009
§ 371 (c)(1),
(2), (4) Date: Jul. 8, 1999

(87) PCT Pub. No.: WO98/30206
PCT Pub. Date: Jul. 16, 1998

(30) Foreign Application Priority Data

Jan. 13, 1997 (SE) .............................................. 9700061

(51) Int. Cl.⁷ .............................. A61K 9/08; A61K 9/10
(52) U.S. Cl. ........................ 424/400; 424/400; 424/401; 424/405; 424/450; 514/937; 514/938; 514/941; 514/943
(58) Field of Search ................. 424/401, 405, 424/400, 450; 514/937, 938, 943, 941

(56) References Cited

U.S. PATENT DOCUMENTS

| | | | | |
|---|---|---|---|---|
| 4,035,513 A | * | 7/1977 | Kumano | 424/359 |
| 5,264,460 A | * | 11/1993 | Jakobson et al. | 514/786 |
| 5,444,041 A | * | 8/1995 | Owen et al. | 514/2 |
| 5,807,573 A | * | 9/1998 | Ljusberg-Wahren et al. | 424/450 |
| 6,013,269 A | * | 1/2000 | El-Nokaly et al. | 424/401 |
| 6,106,860 A | * | 8/2000 | Stuchlik et al. | 424/456 |

FOREIGN PATENT DOCUMENTS

| | | |
|---|---|---|
| EP | 0455391 A3 | 11/1991 |
| GB | 2222770 B | 3/1990 |
| WO | Wo92/18147 | 10/1992 |
| WO | WO97/02042 | 1/1997 |
| WO | 98/05309 * | 2/1998 ............ A61K/9/48 |

OTHER PUBLICATIONS

"Preparation and Surfactant Properties of Diglycerol Esters of Fatty Acids", T. Naveen Kumar et al., *JAOCS*, vol. 66, No. 1 (Jan. 1989) pp. 153–157.

Chemical Abstract No. 97 133 403h, *Pharmaceutical Excipients Based on Glycol and Glycerol Polymers* [Based on *Bull. Tech/Gattefosse* publication by Bernard Glas et al., No. 74 (1981) pp. 41–50].

Chemical Abstract No. 96 168 752c, *Controlled Release Compositions for Administration of Therapeutic Agents to Ruminants* [Based on International Patent Publication No. WO 82/00094, published Jan. 21, 1982, Applicant: Commonwealth Scientific and Industrial Research Organization].

"Lipid Microemulsions for Improving Drug Dissolution and Oral Absorption: Physical and Biopharmaceutical Aspects", Panayiotis P. Constantinides, *Pharmaceutical Research*, vol. 12, No. 11 (1995) pp. 1561–1572.

"Microemulsions in Pharmaceutics", Martin Malmsten, *Handbook of Microemulsion Science and Technology*, P. Kumar and K.L. Mittal, eds., Marcel Dekker, Inc., New York (1999) pp. 755–771.

"Associative Structures of Polyglycerol Ester in Food Emulsions" W. Hemker, *Journal of the American Oil Chemists Society*, vol. 58 (Feb. 1981) pp. 114–119.

* cited by examiner

Primary Examiner—Russell Travers
Assistant Examiner—S Sharareh
(74) Attorney, Agent, or Firm—Burns, Doane, Swecker & Mathis, L.L.P.

(57) ABSTRACT

A controlled release composition for a biologically active material, which composition is liquid or liquid crystalline and comprises at least one medium or long-chain fatty acid ester of diglycerol as a carrier for said biologically active material, said biologically active material being dissolved or dispersed in said carrier. Said composition is especially useful as a medical composition.

31 Claims, 1 Drawing Sheet

CONTROLLED RELEASE COMPOSITION

This application is a 371 of PCT/SE98/00009 filed on Jan. 8, 1998, which claims priority to Swedish application 9700061-6 filed Jan. 13, 1997.

TECHNICAL FIELD

The present invention is within the field of encapsulating biologically active materials primarily in order to obtain a controlled, including sustained, release as well as increased uptake thereof as is desirable in many different technical fields, such as for instance to have a longer lasting or delayed effect of a pharmaceutically active material. More specifically the invention is based on a novel encapsulating or carrier material or system possessing a number of interesting features.

BACKGROUND OF THE INVENTION

It has been known since the 1960's that certain lipids and their analogues can form a variety of aqueous phases and that molecules that are lipophilic, hydrophilic or amphiphilic can be solubilized or dispersed in said phases. This is the basis for application of different lipid phases in drug delivery. The lamellar liquid crystalline phase and its dispersion as liposomes in excess of water is perhaps the best known example in this respect, and liposome encapsulated drugs exist on the market today. According to a more recent development cubic and reversed hexagonal phases have been utilized. A third type of carrier using lipids and lipid analogues is a microemulsion, which has recently been marketed as a carrier for cyclosporin. Furthermore, PCT/SE96/00893 can be referred to, which discloses the use of an L2 phase as a carrier for a cyclosporin.

The carrier systems referred to above are generally based on fatty acid esters of glycerol. As will be explained below the present invention is, however, based on a new carrier system, viz. a certain class of fatty acid esters of diglycerol. In this context it could be mentioned that fatty acids of polyglycerol have hitherto been used as functional additives in foods and in cosmetic formulations. However, to the best of our knowledge, the diglycerol esters upon which the present invention is based have never been disclosed or even suggested as carrier materials. More specifically, the characteristics of those diglycerol esters which by themselves form lipid water phases have never been utilized for controlled release of biologically active agents. Thus, in connection with food applications previous polyglycerol esters have been used to bind water in an oil during frying to stabilize an emulsion or to influence food texture. In connection with cosmetic formulations the previous polyglycerol esters have always been used in combination with other similar molecules, such as sugar esters or polyoxyethylene amphiphiles. Most applications concern stabilization of emulsion structure but sometimes also of gels, solutions and even solids (lipsticks). In other words, the common use of "emulsifiers/stabilizers" never is to achieve release of drugs or similar biologically active compounds.

As concerns diglycerol a detailed study thereof has been reported by Kumar et al. (JAOCS 66 (1989) 153). Diglycerol was first isolated from polymerized glycerol and then esterified with fatty acids. Mono- and diesters were then separated on a silica column. The surfactant properties were characterized by surface tension and studies of emulsion and foam stabilizations were made. However, nothing is mentioned about any formation of liquid aqueous phases or micellar solutions. The only report, to our knowledge, on formation of liquid crystalline phases in connection with polyglycerol esters is a report by Hemker (JAOCS 58 (1981) 114). The binary phase diagrams disclosed, however, merely involve triglycerol and octaglycerol esters and not the diglycerol esters. At all events, said reference does not disclose or suggest the advantageous properties of diglycerol esters utilized in our invention. Furthermore, the triglycerol and octaglycerol esters specifically referred to behave differently from our diglycerol esters.

As prior art reference can also be made to EP 0 455 391, which discloses polyglycerol fatty acid esters for use e.g. in the pharmaceutical field. However, the preparations disclosed therein are granulated, i.e. solid, compositions and do not have all valuable properties possessed by the liquid or liquid crystalline composition according the present invention. Furthermore, EP 0 455 391 is not specifically directed to any diglycerol esters or any valuable properties thereof as compared to other polyglycerol esters.

GENERAL DESCRIPTION OF THE INVENTION

Thus, the present invention is based on the unexpected finding that certain fatty acid esters of diglycerol are highly efficient in solubilizing or dispersing biologically active materials, both as such and in combination with polar liquids. More specifically the present invention is based on the finding that the diglycerol fatty acid esters defined herein can form liquid or liquid crystalline lipid phases of those types which were referred to above in the opening part of our description. Firstly, these phases can be used to protect a biologically active material, for example against degradation in the gastric region, or against oxidation and hydrolysis, e.g. during storage. Furthermore, the uptake of the biologically active material can be improved, particularly penetration through mucous layers and membranes, for instance in oral delivery or in topical delivery, a great advantage being that the systems are bioadhesive. Other advantageous properties to be mentioned are non-irritant and non-toxic properties, which seem to be dependent, at least to some extent, on the length(s) of the hydrocarbon chains. In addition thereto, the previously known lipid phases can be accomplished in a simple way according to the present invention, viz. merely by varying the number or length of the hydrocarbon chains per molecule. In other words the phase properties can be varied successively in a very easy and advantageous way so as to control and optimize the desired delivery of for instance a particular drug.

As to the varying of phase properties it could be added that within the invention it is possible to accomplish diglycerol ester-water (or other polar liquid) phases ranging from the $L_\alpha$-type to the oil-continuous L2-type, the liquid crystalline phases cubic and reversed hexagonal phases lying therebetween. As a consequence thereof it is also possible, by a simple variation of the hydrocarbon chains, to adjust the composition of the system so as to be more or less close to any of these phase transitions. As an example of an interesting advantage in certain applications it could be mentioned that a composition or formulation just on the edge of, or adjacent to, a transition from lamellar to cubic phase represents fusion of cell membranes. Furthermore, if one is very close to a phase transition, a small shift in water content, for example at exposure to the aqueous gastric environment, can induce a fast release of an encapsulated drug through a desired phase transition. Even micellar solutions can be formed in cases of diglycerol esters of the shortest members of the fatty acids referred to. As far as we know, there are no carrier systems previously known which enable such extensive phase variations. Another interesting example is represented by the case where the composition is an L2 phase containing especially diglycerol monoester of fatty acid and which when contacted with water, or other polar liquid, is transformed into a liquid crystalline phase. Such a contact with water (or polar liquid) can take place in the human or animal body or outside the same.

Still another great advantage, which could not be expected from present knowledge about relation between chemical composition and lipid functionality, is the low chain melting temperature of our diglycerol esters as compared to for instance the corresponding monoglycerol ester. Thus, for instance formulations kept at 15° C. with glycerol monoesters of tall oil fatty acids will contain crystals, whereas the corresponding diglycerol ester will not crystallize at all at said temperature. This is a very important characteristic for the intended uses of our novel compositions in that the general stability criterium for a drug formulation is no crystallization at 15° C. to enable room temperature storage or use.

DETAILED DESCRIPTION OF THE INVENTION

Figure 1:
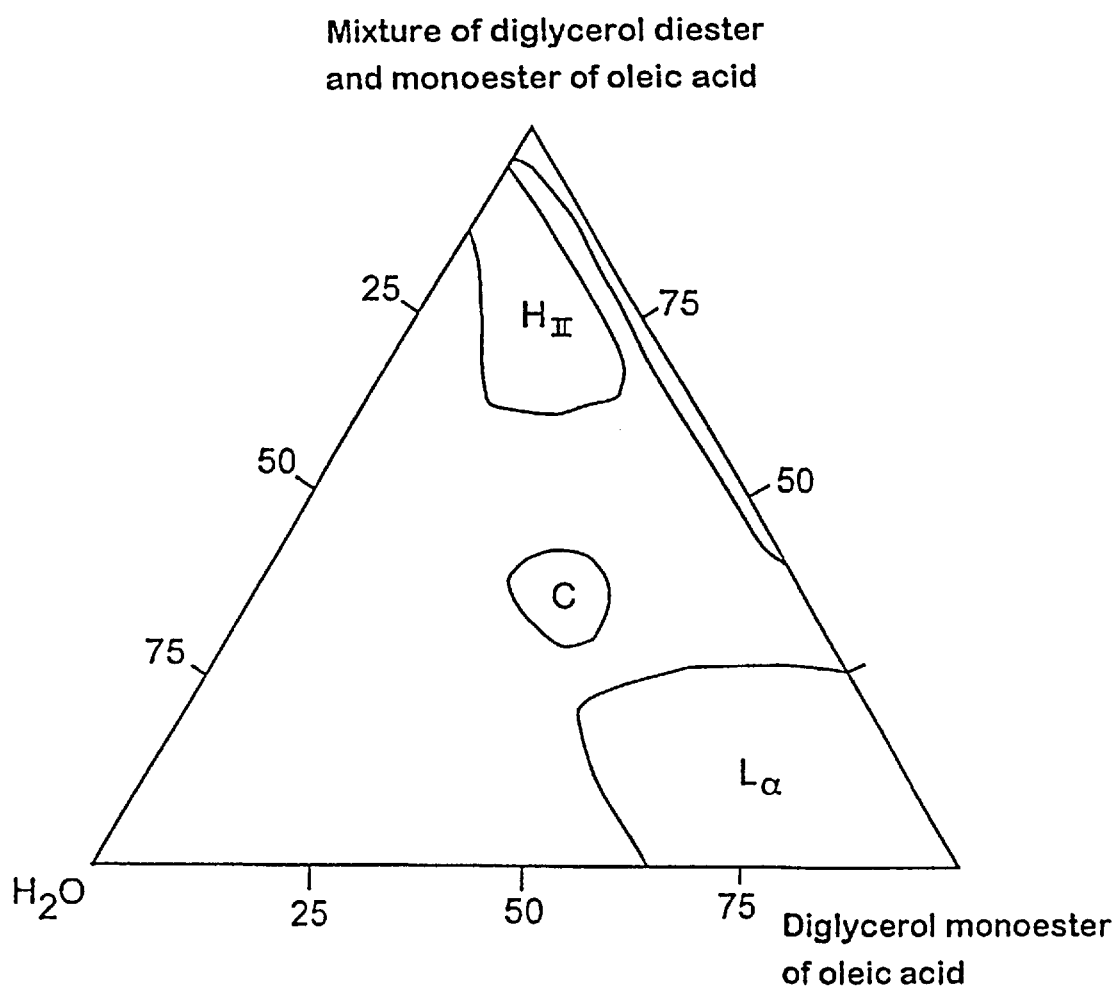
FIG. 1 shows a phase diagram relating to water, diglycerol monoester of oleic acid and a mixture of diglycerol diester and diglycerol monoester of oleic acid at room temperature, the percentages being % w/w.

More specifically the present invention relates to a controlled-release composition for a biologically active material, which composition is liquid or liquid crystalline and comprises at least one medium or long chain fatty acid ester of diglycerol as a carrier for said biologically active material, said biologically active material being dissolved or dispersed in said carrier.

Preferable embodiments of the composition claimed can be presented as follows.

Especially preferable liquid or liquid crystalline compositions according to the invention are selected from the follwing groups: a lamellar liquid phase; a cubic liquid crystalline phase; a reversed hexagonal liquid crystalline phase; and an L2 phase.

In many cases it can be advantageous or even necessary not to use the fatty acid ester of diglycerol as such as said carrier but to include into the composition also a polar liquid. In this respect water may often be a favourable polar liquid but also other polar liquids are useful in accordance with the invention as long as they have the above-mentioned ability of forming any of the previously known well-defined lipid phases with said fatty acid ester(s) of diglycerol. Thus, since the inventive idea has now been disclosed, it should be possible for a person skilled in the art to select a polar liquid for the stated purpose by simple experimentation. However, according to a preferable embodiment of the invention the polar liquid is selected from water, glycerol, ethylene glycol, propylene glycol, ethanol and mixtures thereof.

The inventive idea is generally applicable to any medium or long chain fatty acid to be used in esterifying the diglycerol, the lower and upper limits as to the number of carbon atoms not being strictly rigid. Thus, also in this respect it should be possible for a person skilled in the art to examine whether a specific fatty acid will work satisfactorily or not. Preferably, how-ever, the fatty acids to be used in the composition claimed, or rather in the diglycerol esters, should be fatty acid(s) having in total 6–18 carbon atoms.

Since there may be differences in some respects as to characteristics and achievable results between medium and long chain fatty acids, one favourable group of fatty acids is the group of fatty acids comprising $C_6$–$C_{14}$-fatty acids, while another preferable group of fatty acids can be considered represented by the group of $C_{16}$–$C_{18}$-fatty acids. Said fatty acids can generally be saturated or unsaturated fatty acids.

However, with reference to the $C_6$–$C_{14}$-fatty acids said acids are preferably selected among saturated fatty acids. Preferable examples of such saturated fatty acids are caprylic acid, capric acid, lauric acid and myristic acid.

Said $C_{16}$–$C_{18}$-fatty acids are preferably selected among unsaturated fatty acids, preferable examples thereof being oleic acid, ricinoleic acid, linolic acid and linolenic acid.

Since diglycerol esters are previously known per se, reference can be made to the prior art concerning the preparation of such esters. Generally, however, it can be said that the compounds in question can be prepared by molecular distillation, starting from diglycerol and free fatty acid(s) in appropriate proportions with regard to the desired degree of substitution. As a maximum the diglycerol molecule can be esterified with four fatty acid molecules, and as a minimum with one such molecule. The different esters have different boiling points, and therefore the distillation can be operated to the desired mixture or composition by varying the distillation temperature correspondingly. Mono-, di-, tri- and tetraesterified diglycerols can all be utilized in connection with the present invention, although the mono- and/or diesters are generally preferred. An especially preferable embodiment is represented by an esterified diglycerol wherein the monoester is the major ingredient, i.e. present to more than 50% by weight, preferably more than 70% by weight, more preferably more than 80% by weight, especially more than 90% by weight.

The biologically active material could be any lipophilic, hydrophilic or amphiphilic material, as appropriate. However, preferably it is a lipophilic or amphiphilic material, especially a pharmaceutical material. Examples of such pharmaceutical materials or compounds in connection with which the invention is especially preferable are antibiotics, proteins, peptides, steroids, vitamins, nucleic acids and vaccines. Peptides, or peptide-like molecules, and proteins are of special interest as they are often of low or variable bioavailability.

In the case of charged amphiphilic biologically active materials such materials may well influence upon the formation of the desirable lipid phases. One example of such a material is lidocaine. In order to control or maintain the diglycerol ester phase properties in such a case it is preferable to add a fatty acid to control or neutralize said charge effect.

Thus, according to another preferable embodiment of the invention the composition also contains a fatty acid in an amount sufficient to neutralize the charge effect or to control the phase properties of the composition. The action of said fatty acid is believed to stem from the fact that it is solubilized in the diglycerol ester phases referred to. In practice the addition of said fatty acid can be performed as some kind of titration towards the desired phase.

The fatty acid referred to is preferably selected from the same fatty acids as are used for the diglycerol esters present in the composition, i.e. generally from fatty acids having 6–18 carbon atoms, e.g. 6–14 carbon atoms or 16–18 carbon atoms.

Although pharmaceutical compounds may be of a special interest, the invention is of course also applicable to any other biologically active material for which the inventive ideas could be utilized in any application.

The biologically active material is preferably present in the composition according to the invention in an amount of 0.1–20, more preferably 0.2–10, % by weight, based on the total weight of the composition when dissolved in the carrier. When being dispersed in the carrier the biologically active material is preferably present in the composition in an amount of 0.1–40, more preferably 0.2–20, and most preferably 1–15, % by weight, based on the total weight of the composition. In general terms the composition according to the invention can be prepared in any conventional way, i.e. according to any of those techniques which have previously been utilized for lipid carriers, especially for monoglycerol fatty acid esters. However, further details as to the preparation can be found in the working examples presented below.

As to the exact composition of the liquid or liquid crystalline product of the invention it can be taken from a phase diagram for each and every specific combination to be used. However, generally the amount of water (or other polar liquid) which a lamellar liquid phase contains will be in the range of 0–50%, while a cubic liquid crystalline phase will contain 20–50% thereof, a reversed hexagonal liquid crystalline phase will contain 20–40% thereof and an L2 phase will contain 0–10% thereof, all percentages being expressed as % by weight. The presence of small amounts of charged lipids can increase the swelling of the lipid structure in polar liquids in the case of the cubic and lamellar phases.

Since the novel composition is of special interest in connection with medical uses, another aspect of the invention is represented by a composition as previously defined for use as a medicament for controlled release of said biologically active material, i.e. in the form of a pharmaceutical compound.

The use of the composition is especially interesting for oral or topical delivery of the pharmaceutical compound, a very advantageous characteristic or property of the composition being that it is bioadhesive, as is for instance disclosed in connection with the working examples.

Since the invention is not restricted to the incorporation of a pharmaceutically active material in the composition, still another aspect of the invention is represented by the use of the composition as previously defined for the controlled release of a biologically active non-medical material in any application where the advantages achieved by the invention could be utilized.

Finally, the invention relates to a method of administering to a mammal, especially a human being, the composition as previously defined to the body of said mammal in an amount that is effective for the intended curative or prophylactic treatment. By said method a controlled release of the biologically active material is achieved, together with other advantageous effects as stated above.

EXAMPLES

A carrier in drug delivery will usually be exposed to a water medium, and therefore the phase which is formed by the carrier in excess of water is significant. If taking the oleic acid esters of diglycerol as an example, these esters form four types of aqueous phases in excess of water. With one fatty acid chain the lamellar liquid-crystalline phase ($L_\alpha$) is formed. When the number of chains is increased, one moves successively to $L_\alpha$+cubic phase, pure cubic phase, cubic phase+hexagonal ($H_{II}$) phase, pure $H_{II}$-phase, $H_{II}$-phase+ L2-phase and finally pure L2-phase. It could also be added that when all four hydroxyl groups of the diglycerol are esterified there is formed an oil which does not have any capability of incorporating water. With a decreasing degree of esterification said oil successively passes on to an L2-phase. In this way it is possible to form an L2-phase which can only accomodate a very minor amount of water, for instance 5% (w/w). The same phases and very similar phase boundaries are obtained if water is replaced by any of the other polar liquids stated, i.e. glycerol, ethylene glycol, propylene glycol or ethanol. Therefore, in FIG. 1 a phase diagram is presented which represents water as the polar liquid but which is thus typical in this respect. As can be seen from said diagram it is a phase diagram relating to water, diglycerol monoester of oleic acid and a mixture of diglycerol diester and diglycerol monoester of oleic acid at room temperature, the percentages being % w/w. Unless stated all percentages given herein are % by weight values.

Example 1

Preparation of Diglycerol Fatty Acid Ester

A diglycerol ester of capric acid with the composition presented below was prepared by conventional esterification of capric acid (98% w/w) and diglycerol (95% w/w) followed by a short-path, high-vacuum distillation, referred to as a molecular distillation

| | |
|---|---|
| Diglycerol mono-ester | 73% |
| Diglycerol di-ester | 9% |
| Others | 4% |
| Free diglycerol | 14% |

Example 2

Oral Cyclosporin A Formulation

In the diglycerol ester from Example 1 10% of cyclosporin A was dissolved. The formulation crystallized in a freezer but melted again to a homogeneous liquid at 15° C., which shows that the diglycerol ester from Example 1 was a good vehicle or carrier for cyclosporin A since a therapeutically interesting level of the drug was soluble at room temperature and was independent of said earlier low temperature exposure.

Example 3

Particle Size of Cyclosporin A Formulations Diluted with Water

Two formulations of cyclosporin A, both containing diglycerol ester, were diluted with water (99% w/w) at pH 2.9 and 37° C. The formulations were easily dispersible and the particle sizes of the dispersions were measured on a Mastersizer S. The average particle size was 2.3 μm for formulation A and 1.5 μm for formulation B.

| Formulation A | Formulation B |
|---|---|
| 81% of ester from Example 1 | 90% of ester from Example 1 |
| 10% of cyclosporine A | 10% of cyclosporine A |
| 9% of ethanol | |

This example shows that the composition was easily self-emulsifying which is a proviso for a good oral uptake.

Example 4

Preparation of Diglycerol Ester

The raw materials used in this Example were commercial diglycerol with a purity of 92–95% of diglycerol (linear) and food-grade vegetable fatty acids with a minimum purity of 92%.

The first synthesis step was an esterification reaction of the fatty acids with diglycerol, resulting in an equilibrium mixture of diglycerol mono-esters, diglycerol di-esters, diglycerol tri-esters and possibly traces of diglycerol tetra-esters, combined with small amount of free diglycerol and free fatty acids.

The removal of said free diglycerol and subsequent concentration of the diglycerol mono-esters were performed in several steps while using short-path high-vacuum distillation processes, yielding a product with the following composition (in % by weight):

| | |
|---|---|
| Diglycerol mono-esters | 81.8% |
| Diglycerol di- and tri-esters | 7.3% |
| Monoglycerides | 3.6% |
| Diglycerides | 1.6% |
| Free diglycerol (polyols) | 5.4% |
| Free fatty acids | 0.2% |
| Total | 99.9% |

The fatty acid composition of the diglycerol monooleate used in this example was:

| | |
|---|---|
| Palmitic acid C16 | 0.7% |
| Margaric acid C17 | 0.3% |
| Stearic acid C18 | 2.7% |
| Oleic acid C18:1 | 91.8% |
| Linoleic acid C18:2 | 4.5% |
| Total | 100% |

Chemical characteristics for the product are:

| | |
|---|---|
| Saponification value | 126 |
| Hydroxyl value | 428 |
| Acid value | 0.5 |

Example 5

Bioadhesivity of the Composition

The hexagonal phase of diglycerol monoester of oleic acid, mixture of diglycerol monoester and diglycerol diester of oleic acid, and water 15/75/10% w/w was adhered to human skin at the upper side of the hand in an amount of approximatively 0.2–0.5 g. The hand was held in water with a temperature of approximatively 30° C. for 15 min. The phase was then removed from the skin with a spatula. The hexagonal phase contained 10% of water and swelled in excess of water. The materials collected from the skin were dried to a constant weight over phosphorous pentoxide. The results are presented in the following table:

| Sample | Amount of sample adhered | Contents of lipid in the adhered sample | Contents of lipid in the collected material after drying | % |
|---|---|---|---|---|
| I | 0.2652 g | 0.2387 g | 0.2378 g | 99.6% |
| II | 0.2718 g | 0.2446 g | 0.2424 g | 99.1% |
| III | 0.4043 g | 0.3639 g | 0.3625 g | 99.6% |
| IV | 0.5726 g | 0.5153 g | 0.5144 g | 99.8% |

Example 6

Topical Formulation with Progesterone

| Component | Quantity |
|---|---|
| Progesterone | 40.0% |
| Diglycerolmono-dioleate | 54.0% |
| Diglycerolmonooleate | 6.0% |

The lipids were melted together. The progesterone was dispersed in the lipid to the formation of a homogeneous soft paste. The composition was easily spreadable to a film, which got harder on the addition of water. The composition was easily filled onto a tube.

Example 7

Increased Oral Bioavailability of the Nonapeptide dDAVP

Two groups of rats (n=4 in each group) were gavaged using a soft stomach tube with two formulations of the nonapeptide dDAVP (106.8 µg/g), either as a saline solution or as a lipid vehicle based on diglyceride esters of capric acid. The composition of said lipid vehicle is shown in Table 1. Directly after said gavage of the dDVAP formulations (1.0 ml kg$^{-1}$ body wt), saline was flushed (9.0 ml kg$^{-1}$ body wt) through the same tubing.

The animals were placed in metabolic cages followed by urine colletion for 24 h. Earlier studies have been performed and indicate that urine recovery is a reliable parameter of intestinal absorption of this peptide. The results of the urin recovery of dDAVP was 0.447±0.274% for the lipid vehicle and 0.059±0.057% for the saline solution, which shows an almost 8-fold enhancement of the dDAVP absorption for the lipid vehicle as compared to the saline solution.

TABLE 1

| Ingredient | % by weight |
|---|---|
| tetraester | 0.2% |
| triester | 5.2% |
| diester | 7.5% |
| monoester | 70.2% |
| diglycerol | 5.7% |
| ethanol | 11.1% |

What is claimed is:

1. A controlled-release composition for a biologically active material, which composition is liquid or liquid crystalline and consisting essential of at least one medium or long chain fatty acid ester of diglycerol as a carrier for said biologically active material, wherein said fatty acid of said diglycerol ester is selected from the group consisting of $C_6$–$C_{18}$-fatty acids and mixtures thereof; wherein the fatty acid ester of diglycerol is the only carrier for the biologically active material;

wherein said biologically active material being dissolved or dispersed in said carrier;

wherein said fatty acid ester of diglycerol comprises more than 50% of the monoester thereof; and wherein said liquid or liquid crystalline phase is selected from the group consisting of lamellar liquid crystalline phase, cubic liquid crystalline phase, reversed liquid crystalline phase, homogeneous liquid phase of such a composition that it is transformed into a liquid crystalline phase or micellar solution when contacted with water or any other polar liquid, or mixtures thereof.

2. A composition according to claim 1, which also comprises a polar liquid having the ability of forming a liquid or liquid crystalline phase with said fatty acid ester(s) of diglycerol.

3. A composition according to claim 2, wherein said polar liquid is selected from the group consisting of water, glycerol, ethylene glycol, propylene glycol, ethanol and mixtures thereof.

4. A composition according to claim 1, wherein said fatty acid is selected from $C_6$–$C_{14}$-fatty acids and mixtures thereof.

5. A composition according to claim 1, wherein said $C_6$–$C_{14}$-fatty acids and mixtures thereof are saturated fatty acids.

6. A composition according to claim 5, wherein said fatty acids are selected from the group consisting of caprylic acid, capric acid, lauric acid, myristic acid and mixtures thereof.

7. A composition according to claim 1, wherein said fatty acid is selected from the group consisting of $C_{16}$–$C_{18}$-fatty acids and mixtures thereof.

8. A composition according to claim 7, wherein said $C_{16}$–$C_{18}$-fatty acids and mixtures thereof are unsaturated fatty acids.

9. A composition according to claim 8, wherein said fatty acids are selected from the group consisting of oleic acid, ricinoleic acid, lineolic acid, linolenic acid and mixtures thereof.

10. A composition according to claim 1, wherein said fatty acid ester of diglycerol comprises more than 50% by weight of the monoester thereof.

11. A composition according to claim 1, wherein the biologically active material is selected from amphiphilic and lipophilic materials.

12. A composition according to claim 11, wherein said biologically active material is selected from the group consisting of peptides and proteins.

13. A composition according to claim 11, wherein the amphiphilic and lipophilic materials are pharmaceutical compounds.

14. A composition according to claim 1, wherein said biologically active material is present in an amount of 0.1–20% by weight based on the total weight of the composition, when dissolved in said carrier.

15. A composition according to claim 1, wherein said biologically active material is present in an amount of 0.1–40% by weight based on the total weight of the compositions, when dispersed in said carrier.

16. A composition according to claim 1, wherein the amounts of the ingredients present in the composition are selected so as to get a formulation close to a phase transition.

17. A composition according to claim 16, which contains said fatty acid ester of diglycerol as diglycerol monoester of said fatty acid and is a homogeneous liquid formulation, the composition being such that it is transformed into a liquid crystalline phase or micellar solution when contacted with water or any other of said polar liquids.

18. A composition according to claim 16, wherein the phase transition is a transition from lamellar to cubic phase.

19. A composition according to claim 1, which contains a fatty acid in an amount sufficient to maintain the diglycerol ester phase properties influenced by the biologically active material.

20. A composition according to claim 19, wherein the fatty acid has 6–18 carbon atoms.

21. A composition according to claim 19, wherein the fatty acid has 6–14 carbon atoms.

22. A composition according to claim 19, wherein the fatty acid has 16–18 carbon atoms.

23. A composition as defined in claim 1, wherein said liquid or liquid crystalline phase is selected from the group consisting of a lamellar liquid crystalline phase, a cubic liquid crystalline phase, a reversed hexagonal liquid crystalline phase and an L2 phase.

24. A composition as defined in claim 23, which is a
    a) lamellar liquid phase wherein the amount of polar liquid is in the range of 0–50% by weight;
    b) cubic liquid crystalline phase wherein the amount of polar liquid is in the range of 20–50% by weight; or
    c) reversed hexagonal liquid crystalline phase wherein the amount of polar liquid is 20–40% by weight.

25. A method of using a composition as defined in claim 1 for the controlled release of a biologically active non-medical material, comprising the step of:
    administering the composition to the body of a mammal.

26. A composition according to claim 1, wherein said fatty acid ester of diglycerol comprises more than 70% by weight of the monoester thereof.

27. A composition according to claim 1, wherein said fatty acid ester of diglycerol comprises more than 80% by weight of the monoester thereof.

28. A composition according to claim 1, wherein said fatty acid ester of diglycerol comprises more than 90% by weight of the monoester thereof.

29. A composition according to claim 1, wherein said biologically active material is present in an amount of 0.2–10% by weight, based on the total weight of the composition, when dissolved in said carrier.

30. A composition according to claim 1, wherein said biologically active material is present in an amount of 0.2–20% by weight based on the total weight of the compositions, when dispersed in said carrier.

31. A composition according to claim 1, wherein said biologically active material is present in an amount of 1–15% by weight, based on the total weight of the compositions, when dispersed in said carrier.

* * * * *